US012070485B2

(12) United States Patent
Manenica et al.

(10) Patent No.: US 12,070,485 B2
(45) Date of Patent: Aug. 27, 2024

(54) LIQUID DALBAVANCIN COMPOSITIONS

(71) Applicant: Xellia Pharmaceuticals ApS, Copenhagen (DK)

(72) Inventors: Martina Manenica, Zagreb (HR); Ema Kovacevic, Zagreb (HR); Ernest Mestrovic, Zagreb (HR)

(73) Assignee: Xellia Pharmaceuticals ApS, Copenhagen (DK)

( * ) Notice: Subject to any disclaimer, the term of this patent is extended or adjusted under 35 U.S.C. 154(b) by 0 days.

(21) Appl. No.: 18/484,819

(22) Filed: Oct. 11, 2023

(65) Prior Publication Data

US 2024/0139282 A1 May 2, 2024

Related U.S. Application Data

(60) Provisional application No. 63/518,014, filed on Aug. 7, 2023.

(30) Foreign Application Priority Data

Oct. 12, 2022 (DK) .............................. PA202200932
Feb. 17, 2023 (EP) ..................................... 23157323

(51) Int. Cl.
*A61K 38/14* (2006.01)
*A61K 9/08* (2006.01)
*A61K 31/04* (2006.01)
*A61K 47/26* (2006.01)
*A61K 47/40* (2006.01)
*A61P 31/04* (2006.01)

(52) U.S. Cl.
CPC ................ *A61K 38/14* (2013.01); *A61K 9/08* (2013.01); *A61K 47/26* (2013.01); *A61K 47/40* (2013.01); *A61P 31/04* (2018.01)

(58) Field of Classification Search
None
See application file for complete search history.

(56) References Cited

U.S. PATENT DOCUMENTS 6,858,584 B2   2/2005  Judice
2020/0171124 A1   6/2020  Chandran et al.

FOREIGN PATENT DOCUMENTS

| WO | WO 2004/045637 A1 | 6/2004 |
|---|---|---|
| WO | WO 2016/071495 A1 | 5/2016 |
| WO | WO 2017/194385 A1 | 11/2017 |
| WO | WO 2018/096556 A1 | 5/2018 |
| WO | WO 2023/211501 A1 | 11/2023 |

OTHER PUBLICATIONS

Ament et al., Am. Fam. Physician 65:663-70 (2002) (Year: 2002).*
Stella et al., Toxicologic Pathol. 36:30-42 (2008) (Year: 2008).*
Soriano et al., Exp. Rev. Anti-Infective Ther. 18:415-422 (2020) (Year: 2020).*
Jakaria, Sardar M., et al. Strategies To Stabilize Dalbavancin in Aqueous Solutions; Section 3: The Effects of 2 Hydroxypropyl-β-Cyclodextrin and Phosphate Buffer with and without Divalent Metal Ions. Pharmaceutical Research. 2023. https://doi.org/10.1007/s11095-023-03525-w.
Jakaria, Sardar M., et al. Strategies To Stabilize Dalbavancin in Aqueous Solutions; Section-1: the Effects of Metal Ions and Buffers. Pharmaceutical Research. 2023. https://doi.org/10.1007/s11095-023-03588-9.
Jakaria, Sardar M., et al. Strategies to stabilize dalbavancin in aqueous solutions: Section 4—identification of heat degradation products in 2-hydroxypropyl-β-cyclodextrin and divalent metal ion solutions at pH 4.5 and 7.0. AAPS Open, 9:8, 2023. https://doi.org/10.1186/s41120-023-00076-7.
Jakaria, Sardar M., et al. Glycopeptide antibiotic drug stability in aqueous solution, AAPS Open, 8:20, 2022. https://doi.org/10.1186/s41120-022-00067-0.
Jakaria, Sardar M., et al. A Systematic Degradation Kinetics Study of Dalbavancin Hydrocholoride Injection Solutions. Journal of Pharmaceutical Sciences, 112(7), pp. 1872-1887, 2023; https://doi-org/10.1016/j.xphs2023.02.0006.
Supplemental Material (SM) for Jakaria et al., "A Systematic Degradation Kinetics Study of Dalbavancin Hydrochloride Injection Solutions", Journal of Pharmaceutical Sciences, 112(7), pp. 1872-1887, 2023; https://doi-.org/10.1016/j.xphs2023.02.0006.
Jakaria, Sardar M. A Systematic Study of Stabilizing Lipoglycopeptide (Dalbavancin) Therapeutic Drugs in Aqueous Solution. Dissertation submitted to The Faculty of the College of Science of Northeastern University, published Jun. 14, 2023.
Loftsson, Thorsteinn, et al., "The complexation efficiency," J Incl Phenom Macrocycl Chem (2007) 57:545-552.
Stella, Valentino J., and Rajewski, Roger A., "Sulfobutylether-β-cyclodextrin," International Journal of Pharmaceuticals, 583 (2020) 119396.

\* cited by examiner

*Primary Examiner* — Thea D'Ambrosio
(74) *Attorney, Agent, or Firm* — Karen A. LeCuyer; DeWitt LLP

(57) ABSTRACT

The present disclosure relates to a stable aqueous composition of dalbavancin, the process for making such compositions and use of such compositions for treatment of a patient in need thereof.

9 Claims, No Drawings

LIQUID DALBAVANCIN COMPOSITIONS

CROSS-REFERENCE TO RELATED APPLICATIONS

This application claims priority to Danish application PA202200932, filed Oct. 12, 2022, European Application EP 23157323.9, filed Feb. 17, 2023, and U.S. Provisional Application 63/518,014 filed Aug. 7, 2023, which are incorporated herein by reference in their entirety.

FIELD OF THE INVENTION

The present disclosure relates to stable aqueous composition of dalbavancin, the process for making such compositions and use of such compositions for treatment of a patient in need thereof. Such compositions provide good stability.

BACKGROUND

Dalbavancin is a semisynthetic lipoglycopeptide and exerts its bactericidal effect by disrupting cell wall biosynthesis. It binds to the D-alanyl-D-alanyl residue on growing peptidoglycan chains and prevents transpeptidation from occurring, preventing peptidoglycan elongation and cell wall formation.

Dalbavancin is manufactured by fermentation of a selected Nonomuraea strain to generate the natural glycopeptide complex A-40926. This precursor is then selectively esterified at the carboxyl group of its sugar moiety, its peptidyl carboxyl group is amidated and the ester of the N-acylaminoglucuronic acid carboxyl group is saponified. The outcome is a compound mixture of two closely related structural families—A and B—that can be further subdivided into a total of five subtypes (Table 1).

The structure of dalbavancin is shown below:

TABLE 1

| Dalbavancin subtypes | | |
|---|---|---|
| Homolog | Alkyl sidechain of N-acylaminoglucuronic acid ($R^1$) | Amino-terminal substituent ($R^2$) |
| $A_0$ | $CH(CH_3)_2$ | H |
| $A_1$ | $CH_2CH_2CH_3$ | H |
| $B_0$ | $CH_2CH(CH_3)_2$ | H |
| $B_1$ | $CH_2CH_2CH_2CH_3$ | H |
| $B_2$ | $CH_2CH(CH_3)_2$ | $CH_3$ |

Dalbavancin is marketed under the tradename DALVANCE® in US and XYDALBA® in Europe. The marketed product is a lyophilized powder containing dalbavancin hydrochloride, lactose monohydrate and mannitol. It may also contain sodium hydroxide and/or hydrochloric acid. The lyophilized powder needs to be reconstituted and diluted prior to administration to a patient. The package insert for DALVANCE® (dalbavancin) for injection instructs the user to use either Sterile Water for Injection, USP, or 5% Dextrose Injection, USP, for reconstitution of the lyophilized product and subsequently to dilute only with 5% Dextrose Injection, USP, to a final concentration of 1 mg/mL to 5 mg/ml. The total time from reconstitution to dilution to administration should not exceed 48 hours.

Dalbavancin is marketed for treatment of adult and pediatric patients with acute bacterial skin and skin structure infections (ABSSSI) caused by designated susceptible strains of Gram-positive microorganisms.

What is needed are stable liquid compositions of dalbavancin that do not need reconstitution and/or dilution prior to administration and are stable over a long period of time.

SUMMARY

It has been found that the liquid compositions of dalbavancin described herein possess surprisingly improved stability. In particular, it has been found certain liquid compositions that are stable for a certain period of time at room temperature.

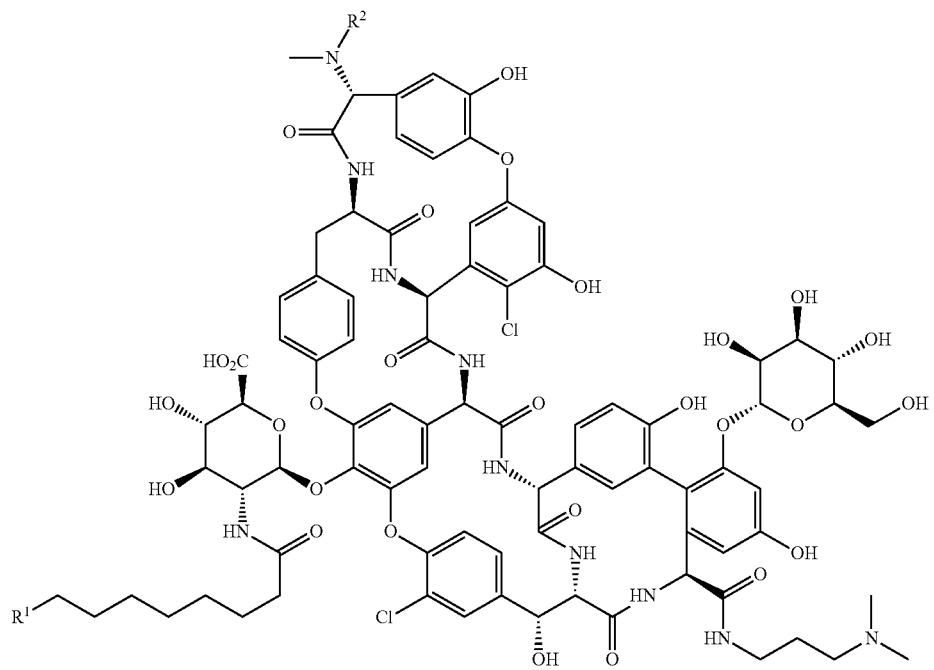

It has been found that an aqueous solution of dalbavancin comprising at least one excipient selected from N-acetyl-D-amino acids or N-acetyl-Glycine and/or at least one solubilizing agent is stable for certain period of time.

It has also been found that these aqueous solutions of dalbavancin will have low levels of mannosyl aglycon impurity.

It has been found that these aqueous solutions of dalbavancin in water have good chemical and physical stability for a certain period of time at room temperature.

DETAILED DESCRIPTION (INCLUDING DEFINITIONS)

As used herein, the terms "pharmaceutical composition", "pharmaceutical formulation", "composition" and "formulation" are used interchangeably.

By the term "aqueous solution" is understood any solution in which water is present at or above 50% v/v, such as, e.g., a solution comprising from about 50% v/v to about 100% v/v water. Accordingly, aqueous solutions include solutions comprising about 50% v/v or more, about 60% v/v or more, about 70% v/v or more, about 75% v/v or more, about 80% v/v or more, about 85% v/v or more, about 90% v/v or more, about 95% v/v or more or about 100% v/v water.

"Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions) may be formulated according to the known art using suitable dispersing, wetting, suspending agents and/or solubilizing agents.

The term "ready-to-administer" is synonymous with "ready-to-infuse" or "ready-to-inject" and is not to be read as the term "ready-to-use" aqueous solution.

The term "ready-to-use" includes aqueous preconcentrates which require a single step of dilution with an aqueous diluent fluid such as water for injection or saline before administration. The term "ready-to-administer" is also distinguished from lyophilized products that require two steps, a first step of reconstitution to form a preconcentrate and then a second step where the preconcentrate is subjected to dilution with an aqueous infusion fluid. The "ready-to-administer" parenteral dosage form according to the present disclosure avoids the inconvenience of reconstituting or diluting a concentrated parenteral formulation into infusion diluents prior to infusion, as well as eliminates the risk of any potential calculation or dilution error as well as risks of microbiological contamination during handling.

The aqueous dalbavancin formulations described herein may be a ready-to-use or a ready-to-administer solution that may be packed in a flexible plastic container or it may be packed in a vial or a bottle.

As used herein, the term "flexible plastic container" means flexible polymeric infusion bags or other polymeric containers. Exemplary flexible plastic containers are made of polyolefins, such as polyethylene, polypropylene, copolymers and derivatives thereof, with or without other additives.

Typically, the compounds of the present disclosure are administered in an amount effective to treat a condition as described herein. The compounds of the present disclosure are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The term "therapeutically effective amount" as used herein refers to that quantity of a compound or pharmaceutical composition that is sufficient to result in a desired activity upon administration to a subject in need thereof. An "effective amount" means the amount of a compound or pharmaceutical composition according to the present disclosure that, when administered to a patient for treating an infection or disease is sufficient to effect such treatment. The "effective amount" will vary depending on the active ingredient, the state of infection, disease or condition to be treated and its severity, and the age, weight, physical condition and responsiveness of the mammal to be treated.

Dalbavancin is prone to degradation and the most important impurity is the mannosyl aglycon (MAG) impurity shown below:

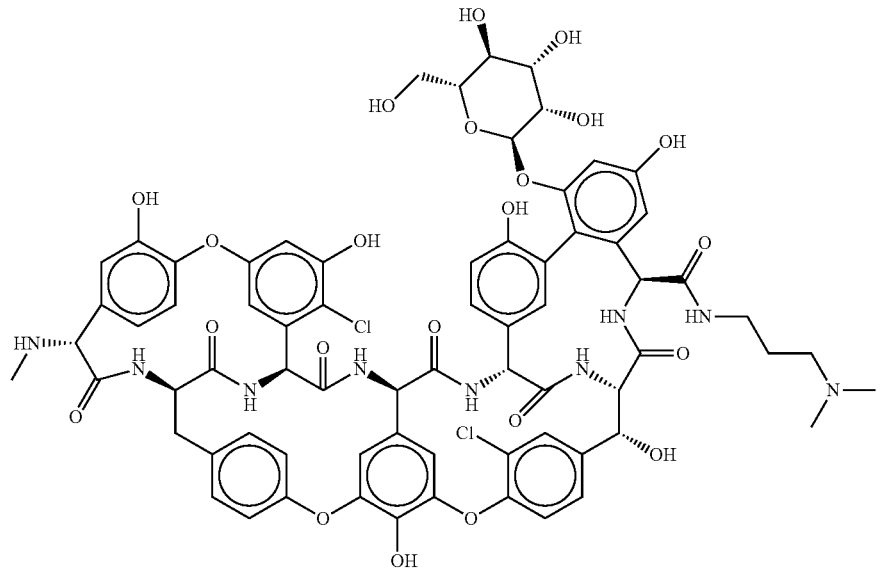

The term "stability", "chemical stability" or "stable" means that the product, composition or formulation exhibits an acceptable amount of dalbavancin being present, or not more than a certain amount of dalbavancin has degraded after a certain period of time. Accordingly, in a stable product, solution or formulation, unacceptable degradation of the active agent is avoided.

Stability can be presented as the purity or assay of dalbavancin in a composition according to the disclosure. If the composition initially contains dalbavancin of a certain purity or assay, the stability of the composition will be reflected by a decrease in the same in the product, formulation or composition over time, where a stable composition would contain the dalbavancin of a specified chromatographic purity or assay after a predetermined time period. For example, the formation of MAG is reduced in a stable product.

For example, a stable composition can be one which has not more than a 1%, 2%, 3%, 4%, 5%, 6%, 7%, 8%, 9%, 10%, assay decrease/drop of dalbavancin after a predetermined time period analyzed by liquid chromatography, e.g., HPLC, UHPLC, or LC/MS.

Accordingly, "stability" may also be defined by the amount of total or individual impurities generated after a certain period of time. The amount of impurities being present may be expressed as a percentage, for example as a peak-area percentage of a HPLC chromatogram or calculated according to standard solution.

The degradation of dalbavancin to produce mannosyl aglycon impurity may be identified based on the relative retention time (RRT) of dalbavancin and mannosyl aglycon impurity in an HPLC chromatogram.

As used herein, the increase (delta) in mannosyl aglycon impurity is measured from the time of preparation of the formulation and storage through the specified time, e.g., 3 months and 6 months.

For example, a stable composition can be one which has not more than a 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0% increase in the amount of mannosyl aglycon impurity after storage at 25° C. for 3 months.

In addition to chemical stability, the physical stability of the composition may be monitored. Physical stability is defined as the appearance of the formulation and includes visual inspection of precipitation, clarity, and color of the solution.

Color can be determined spectrophotometrically by using the L*a*b* color space method and calculating the Δ in accordance with USP <1061>.

In liquid ready-to-administer pharmaceutical products it is important to have formulations without any visible particles or precipitation.

In an aspect, the aqueous dalbavancin formulations according to the present disclosure are stable at a temperature of from 2° C. to 8° C. for a certain period of time. In an aspect, the aqueous dalbavancin formulations according to the present disclosure are stable under room temperature conditions for a certain period of time. By the term "room emperature" used herein is meant from 20° C. to 27° C. In an aspect, the aqueous dalbavancin formulations according to the present disclosure are stable at 40° C. for a certain period of time. In an aspect, the aqueous dalbavancin formulations described herein are stable over time periods of 7 days (1 week), 14 days (2 weeks), 30 days (1 month), 60 days (2 months), 3 months, 4 months, 180 days (6 months), 9 months, 12 months (1 year), 14 months, 16 months, 18 months, 20 months, 24 months or more at certain specified temperature conditions.

The formulations disclosed herein may be sterilized by known means. Such known means in the art comprise, for example, sterile filtration.

The formulations disclosed herein are suitable for parenteral administration.

The term "pharmaceutically acceptable salt" refers to a salt prepared by combining a compound of the present disclosure with an acid whose anion, or a base whose cation, is generally considered suitable for use in humans.

The term "dalbavancin" as used herein means dalbavancin or a pharmaceutically acceptable salt of dalbavancin. Dalbavancin is a mixture of two closely related structural compound families—A and B—that can be further subdivided into a total of five subtypes, as shown in the table above. $B_0$ is the main component of the mixture and the components $A_0, A_1, B_1$ and $B_2$ are present in lower amounts. Pharmaceutically acceptable salts of dalbavancin may be salts derived from inorganic or organic acids.

In one aspect the pH of the aqueous dalbavancin formulations is in the range from 3.0-6.5. In an aspect, the pH is in the range of 4.0-6.5. In another aspect the pH is in the range of 5.0-6.0. In another aspect the pH is 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4 or 6.5.

"pH" is the conventional measurement unit of hydrogen ion activity in aqueous or other liquid solutions at room temperature, unless another temperature is specified.

In an aspect, pH values are given for the formulations just after preparation, which means at the start of the stability testing.

The pH of the formulation may be adjusted in any suitable manner. The pH may be adjusted with one or more pH adjusting agents, which may be selected from acids or bases. Examples of pH-adjusting agents include hydrochloric acid and sodium hydroxide and combinations thereof.

In one aspect, the aqueous dalbavancin formulations do not comprise a buffer.

In one aspect, the aqueous dalbavancin formulations do not comprise phosphate buffer.

In one aspect, the aqueous dalbavancin formulations do not comprise acetate buffer.

In one aspect, the aqueous dalbavancin formulations do not comprise citrate buffer.

For intravenous products to be acceptable for administration to humans, such products must have adequate osmolality.

The aqueous dalbavancin formulations described herein may optionally comprise an osmolality adjusting agent. The osmolality adjusting agent may be dextrose.

In one aspect, the osmolality adjusting agent is dextrose.

In an aspect, the concentration of an osmolality adjusting agent in the product is in the amount to provide an iso-osmotic ready-to-administer or ready-to-use product.

In an aspect, the aqueous dalbavancin formulations have an osmolality within the physiological osmolality of blood. According to the literature, and as used herein, the physiological osmolality of blood is in the range of 270 to 340 mOsmol/kg.

In an aspect, the concentration of an osmolality adjusting agent in the aqueous dalbavancin formulations should be in the amount to achieve an osmolality of the product within the targeted range of 270 to 340 mOsmol/kg.

In an aspect, the aqueous dalbavancin formulations are both isotonic and have an osmolality within the physiological osmolality of blood as described above.

In an aspect, the composition described herein includes an N-acetyl-D-amino acid.

N-acetyl-D-amino acids are compounds represented by the following structure

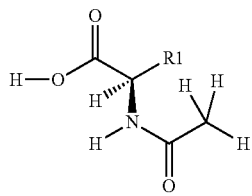

wherein R1 is a side chain of an α-amino acid.

The α-amino acids include Alanine, Arginine, Asparagine, Aspartic acid, Cysteine, Glutamic acid, Glutamine, Histidine, Isoleucine, Leucine, Lysine, Methionine, Phenylalanine, Proline, Serine, Threonine, Tryptophan, Tyrosine, Valine and Ornithine.

The term "N-acetyl-D-amino acids" is also meant to cover any salt thereof, especially pharmaceutically acceptable salts.

N-acetyl-glycine is a compound represented by the following structure

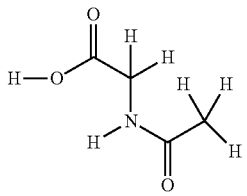

It can exist as an acid or in deprotonated form. The term "N-acetyl-glycine" is also meant to include salts thereof, especially pharmaceutically acceptable salts.

The term "solubilizing agent" is an agent included in the formulation and that helps dalbavancin solutions to remain clear such that no precipitate is seen in the solution. Solubilizing agents include organic molecules, for example such compounds as poly-amino acid based amphiphilic polymers, polysorbates, castor oils, sodium cholesteryl sulfate (SCS), polyvinylpyrrolidone (povidone, PVP), polyoxyl-15-hydroxystearat, N-methyl 2-pyrrolidone (NMP), 2-pyrrolidone, diacylglycerols, monoglycerols, propylene glycol, polyethylene glycol (PEG) and cyclodextrins, for example PEG 400 and hydroxypropyl beta cyclodextrin, as well as combinations of solubilizing agents.

Described herein are stable liquid dalbavancin compositions. In one aspect the composition comprises dalbavancin hydrochloride.

The concentration of dalbavancin in the composition may be in the range of 1 mg/ml to 25 mg/ml. In one aspect the concentration of dalbavancin is in the range of 1 mg/ml to 10 mg/l, 1 mg/ml to 7 mg/ml, or 3 mg/ml to 6 mg/ml. In an aspect, the concentration of dalbavancin is in the range of 4 mg/ml to 6 mg/ml. In another aspect, the concentration of dalbavancin is 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, 5.0 mg/ml, 5.1 mg/ml, 5.2 mg/ml, 5.3 mg/ml, 5.4 mg/ml, 5.5 mg/ml, 5.6 mg/ml, 5.7 mg/ml, 5.8 mg/ml, 5.9 mg/ml or 6.0 mg/ml. In yet another aspect, the concentration of dalbavancin is 5 mg/ml. In an aspect, the concentration of dalbavancin is in the range of 10 mg/ml to 25 mg/ml. In one aspect, the concentration of dalbavancin is in the range of 15 mg/ml to 22 mg/ml. In another aspect, the concentration of dalbavancin is in the range of 18 mg/ml to 22 mg/ml. In another aspect, the concentration of dalbavancin is 18 mg/ml, 19 mg/ml, 20 mg/ml, 21 mg/ml or 22 mg/ml.

When specific amounts or ranges of amounts of dalbavancin are given in this application, all values are calculated based on dalbavancin base.

In an aspect, the composition comprises dalbavancin hydrochloride, a cyclodextrin, and water.

In an aspect, the cyclodextrin is hydroxypropyl beta cyclodextrin.

Hydroxypropyl-beta-cyclodextrin is a partially substituted poly(2-hydroxpropyl) ether of beta-cyclodextrin. In one aspect, the molar substitution of hydroxypropyl beta cyclodextrin is 0.4-1.5.

In one aspect, the molar substitution of hydroxypropyl beta cyclodextrin is 0.5-1.1.

In another aspect, the molar substitution of hydroxypropyl beta cyclodextrin is 0.6-1.0.

In another aspect, the molar substitution of hydroxypropyl beta cyclodextrin is 0.6-0.9.

In another aspect, the molar substitution of hydroxypropyl beta cyclodextrin is 0.5, 0.6, 0.7, 0.8, 0.9, 1.0 or 1.1.

In an aspect, the molar ratio of dalbavancin to hydroxypropyl beta cyclodextrin is in the range of 1:0.5 to 1:10.

In an aspect, the molar ratio of dalbavancin to hydroxypropyl beta cyclodextrin is in the range of 1:0.5 to 1:5.

In an aspect, the molar ratio of dalbavancin to hydroxypropyl beta cyclodextrin is in the range of 1:0.6 to 1:2.

In an aspect, the molar ratio of dalbavancin to hydroxypropyl beta cyclodextrin is in the range of 1:0.6 to 1:1.

In an aspect, the molar ratio of dalbavancin to hydroxypropyl beta cyclodextrin is in the range of 1:0.7 to 1:0.9.

In an aspect, the molar ratio of dalbavancin to hydroxypropyl beta cyclodextrin is 1:0.5, 1:0.6, 1:0.7, 1:0.8, 1:0.9, 1:1, 1:2, 1:3, 1:4 or 1:5.

In an aspect, the composition comprises dalbavancin, an N-acetyl-D-amino acid or N-acetyl-glycine, and water.

In an aspect, the N-acetyl-D-amino acid is selected from N-acetyl-D-alanine, N-acetyl-D-leucine, N-acetyl-D-methionine or a combination thereof. In one aspect the N-acetyl-D-amino acid is N-acetyl-D-alanine.

In an aspect, the molar ratio of dalbavancin to N-acetyl-D-amino acid may be in the range of 1:1 to 40:1.

In an aspect, the molar ratio of dalbavancin to N-acetyl-glycine may be in the range of 1:1 to 40:1.

In an aspect, the composition comprises dalbavancin and a mixture of an N-acetyl-D-amino acid and a solubilizing agent.

In an aspect, the composition comprises dalbavancin and a mixture of an N-acetyl-D-amino acid and a solubilizing agent, wherein the N-acetyl-D-amino acid is N-acetyl-D-alanine.

In an aspect, the composition comprises dalbavancin and a mixture of an N-acetyl-D-amino acid and a solubilizing agent, wherein the solubilizing agent is PEG.

In an aspect, the composition comprises dalbavancin and a mixture of an N-acetyl-D-amino acid and a solubilizing agent, wherein the solubilizing agent is PEG 400.

In an aspect, the composition comprises dalbavancin and a mixture of an N-acetyl-D-amino acid and a solubilizing agent, wherein the solubilizing agent is a cyclodextrin.

In an aspect, the composition comprises dalbavancin and a mixture of an N-acetyl-D-amino acid and a solubilizing agent, wherein the solubilizing agent is hydroxypropyl beta cyclodextrin.

In an aspect, the composition comprises dalbavancin and a mixture of an N-acetyl-D-amino acid and a solubilizing agent, wherein the N-acetyl-D-amino acid is N-acetyl-D-alanine and the solubilizing agent is PEG.

In an aspect, the composition comprises dalbavancin and a mixture of an N-acetyl-D-amino acid and a solubilizing agent, wherein the N-acetyl-D-amino acid is N-acetyl-D-alanine and the solubilizing agent is PEG 400.

In an aspect, the composition comprises dalbavancin and a mixture of an N-acetyl-D-amino acid and a solubilizing agent, wherein the N-acetyl-D-amino acid is N-acetyl-D-alanine and the solubilizing agent is a cyclodextrin.

In an aspect, the composition comprises dalbavancin and a mixture of an N-acetyl-D-amino acid and a solubilizing agent, wherein the N-acetyl-D-amino acid is N-acetyl-D-alanine and the solubilizing agent is hydroxypropyl beta cyclodextrin.

In an aspect, the molar ratio of dalbavancin to N-acetyl-D-alanine to hydroxypropyl beta cyclodextrin is 1:0.5:0.5 to 1:10:4.

In an aspect, the molar ratio of dalbavancin to N-acetyl-D-alanine to hydroxypropyl beta-cyclodextrin is 1:0.1:0.1 to 1:10:4.

In an aspect the composition comprises dalbavancin and a mixture of N-acetyl-D-alanine and hydroxypropyl beta cyclodextrin, wherein the molar ratio between dalbavancin and N-acetyl-D-alanine is 1:0.1 to 1:10; 1:0.5 to 1:10; 1.1 to 1:10; 1:1 to 1:4.5; 1:1 to 1:3; 1:4 to 1:6; 1:4.5 to 1:6; 1:6 to 1:10; 1:7 to 1:10 or 1:8 to 1:10.

In an aspect, the composition comprises dalbavancin and a mixture of N-acetyl-D-alanine and hydroxypropyl beta cyclodextrin, wherein the molar ratio between dalbavancin and hydroxypropyl beta cyclodextrin is 1:1 to 1:2.

In an aspect, the aqueous solution comprises dalbavancin and a mixture of N-acetyl-D-alanine and hydroxypropyl beta cyclodextrin, wherein the molar ratio between dalbavancin and hydroxypropyl beta cyclodextrin is 1:1 to 1:2; and wherein the molar ratio between dalbavancin and N-acetyl-D-alanine is 1:1 to 1:10; and wherein the concentration of dalbavancin is from 1 mg/ml to 25 mg/ml.

In an aspect, the aqueous solution comprises dalbavancin and a mixture of N-acetyl-D-alanine and hydroxypropyl beta cyclodextrin, wherein the molar ratio between dalbavancin and hydroxypropyl beta cyclodextrin is 1:1 to 1:2; and wherein the molar ratio between dalbavancin and N-acetyl-D-alanine is 1:1 to 1:10; and wherein the concentration of dalbavancin is from 1 mg/ml to 7 mg/ml.

In an aspect, the aqueous solution comprises dalbavancin and a mixture of N-acetyl-D-alanine and hydroxypropyl beta cyclodextrin, wherein the molar ratio between dalbavancin and hydroxypropyl beta cyclodextrin is 1:1 to 1:2; and wherein the molar ratio between dalbavancin and N-acetyl-D-alanine is 1:1 to 1:10; and wherein the concentration of dalbavancin is from 15 mg/ml to 22 mg/ml.

In an aspect, the aqueous dalbavancin solution has less than an 8% increase of the mannosyl aglycon impurity as measured by HPLC.

In an aspect, the aqueous dalbavancin solution has less than a 2% increase of the mannosyl aglycon impurity as measured by HPLC after storage at room temperature for 3 months.

In an aspect, the aqueous dalbavancin solution has less than a 1.5% increase of the mannosyl aglycon impurity as measured by HPLC after storage at room temperature for 3 months.

In one aspect the compositions mentioned above can be used for treatment of adult and pediatric patients with acute bacterial skin and skin structure infections (ABSSSI) caused by designated susceptible strains of Gram-positive microorganisms.

EXAMPLES (METHODS, RESULTS, DISCUSSION)

After preparation, the initial time point level of active pharmaceutical ingredient and impurities were determined by high performance liquid chromatography (HPLC) and afterwards containers were loaded into stability chambers at different storage conditions, 40° C. and 25° C.

In order to determine the stability of active pharmaceutical ingredient in formulations according to the present disclosure, containers were taken from stability chambers at various time points, such as 28 days, 1 month, 2 months, 3 months, 6 months etc. and analyzed by HPLC.

The assay for active pharmaceutical ingredient was determined by a gradient HPLC method using internal standards and a DAD detector. Impurities were determined by using the same HPLC method with amount determined by area percentage. Parallel to assay and impurities, component distribution is determined for the five main homologues ($A_0$, $A_1$, $B_0$, $B_1$ and $B_2$) also as an area percentage method. In all cases, a reverse-phase C18 column was used.

HPLC Assay and Impurities Method

Mobile phase A: mixture phosphate buffer and acetonitrile (85/15)

Mobile phase B: mixture phosphate buffer and acetonitrile (35/65)

Mode: LC

Detector: UV 230 nm.

Column: 2.1×5 mm; 3.5 μm packing

Column temperature: 45° C.

Samples are prepared by dilution to 0.3 mg/mL. Every sample sequence is run with injections of internal impurities ID standards as with repeated injections of blank diluent solution. The system is regularly washed because of possible back-pressure increases.

Labeled amount of dalbavancin in percentage is calculated:

$$\text{Assay \%} = \left(\frac{A_S}{A_{std}}\right) \times \left(\frac{c_{std}}{c_s}\right) \times 100$$

$A_s$—peak response of dalbavancin (as a sum of five homologues) from the sample solution $A_{std}$—peak response of dalbavancin (as a sum of five homologues) from the standard solution $c_{std}$—concentration of dalbavancin in the standard solution (mg/mL)

$c_s$—nominal concentration of dalbavancin in the sample solution (mg/mL)

The content of impurities is given as area % of the total area, calculated using the following equation:

$A_i$—peak response of an impurity from the sample solution $A_{tot}$—sum of all peak responses from the sample solution $$Hom\ \% = \left(\frac{A_h}{A_d}\right) \times 100$$

$A_h$—peak response of a homologue from the sample solution $A_d$—sum of all homologue peak responses (A0, A1, B0, B1 and B2) from the sample solution Preparation of Exemplary Formulation Water for Injection or 5% dextrose solution (90% of final volume) was added into a vessel and stirring was started.

The excipients required for the different formulations were added. Dalbavancin hydrochloride was added in an amount to get a final concentration of 5 mg/ml. The solution was stirred until all dry components were dissolved.

pH was adjusted to target pH value by adding in the needed amount of HCl or NaOH (1 M solution). Additional Water for Injection or 5% dextrose solution was added into the solution to reach final volume. The solution was filtrated through 0.22 um filter and filled in containers such as glass vials or plastic bags.

Example 1

This example shows the change in mannosyl aglycon impurity in a formulation of 5 mg/ml of dalbavancin hydrochloride including N-acetyl-D-alanine (NADA) in Water for Injection at different pHs. Data shown is after storage for 3 months and 6 months at 25° C.

TABLE 2

Change in mannosyl aglycon impurity in a formulation with NADA

| Amount of NADA mg/ml | Molar ratio Dalbavancin:NADA | pH | Time point | Δ mannosyl aglycon impurity/% |
|---|---|---|---|---|
| 0 | | 3 | 3 Months | 4.3 |
| | | | 6 Months | 7.8 |
| 13.6 | 1:38 | 3 | 3 Months | 2.0 |
| | | | 6 Months | 4.0 |
| 0 | | 4 | 3 Months | 2.3 |
| | | | 6 Months | 4.3 |
| 3.6 | 1:10 | 4 | 3 Months | 2.0 |
| | | | 6 Months | 3.7 |
| 0 | | 5 | 3 Months | 1.9 |
| | | | 6 Months | 3.3 |
| 0.36 | 1:1 | 5 | 3 Months | 1.3 |
| | | | 6 Months | 2.8 |

Example 2

This example shows the change in mannosyl aglycon impurity in a formulation of 5 mg/ml of dalbavancin hydrochloride including hydroxypropyl beta cyclodextrin in Water for Injection (WFI) at pH 4. Data shown is after storage for 3 months and 6 months at 25° C. and for 4 weeks at 40° C.

TABLE 3

Change in mannosyl aglycon impurity in a formulation with hydroxypropyl beta cyclodextrin

| Composition | Time point | ° C. | Δ mannosyl aglycon impurity/% |
|---|---|---|---|
| Dalbavancin in WFI; pH 4 (CONTROL) | 3 Months | 25 | 2.3 |
| | 6 Months | 25 | 4.3 |
| Dalbavancin in WFI hydroxypropyl beta cyclodextrin (HPBC) Molar ratio dalbavancin:HPBC 1:4 pH 4 | 3 Months | 25 | 1.0 |
| | 6 Months | 25 | 2.1 |
| Dalbavancin in WFI; pH 4 (CONTROL) | 4 weeks | 40 | 5.7 |
| Dalbavancin in WFI hydroxypropyl beta cyclodextrin (HPBC) Molar ratio dalbavancin:HPBC 1:4 pH 4 | 4 weeks | 40 | 3.9 |

Example 3

This example shows the change in mannosyl aglycon impurity in a formulation of 5 mg/ml of dalbavancin hydrochloride including a combination of hydroxypropyl beta cyclodextrin and NADA in 5% dextrose solution at pH 4. The table shows the data after 3 months at 25° C.

TABLE 4

Change in mannosyl aglycon impurity in a formulation with NADA and hydroxypropyl beta cyclodextrin

| Composition number | Molar ratio of NADA to Dalbavancin | Molar ratio of hydroxypropyl beta cyclodextrin to Dalbavancin | Δ mannosyl aglycon impurity/% |
|---|---|---|---|
| 044-5 | 0 | 0 | 2.7 |
| 044-6 | 10:1 | 0 | 1.7 |
| 044-7 | 0 | 2:1 | 0.7 |
| 044-15 | 1.25:1 | 1:1 | 0.5 |
| 044-16 | 8.75:1 | 1:1 | 0.5 |

Example 4

This example shows the change in mannosyl aglycon impurity in a formulation of 5 mg/ml of dalbavancin hydrochloride including different molar ratios of hydroxypropyl beta cyclodextrin in 5% dextrose solution at pH 4. The table shows the data after 3 months at 25 degrees Celsius.

TABLE 5

Change in mannosyl aglycon impurity in a formulation with hydroxypropyl beta cyclodextrin in 5% dextrose solution at pH 4

| Exp. | Molar ratio Dalbavancin:hydroxypropyl beta cyclodextrin | Δ mannosyl aglycon impurity/% |
|---|---|---|
| 103 | 1.0:1.2 | 0.71 |
| 101 | 1.0:1.0 | 0.68 |
| 122 | 1.0:0.8 | 0.54 |
| 128 | 1.0:0.5 | 0.90 |
| 127 | 1.0:0.2 | 1.80 |

Example 5

This example shows the change in mannosyl aglycon impurity in a formulation of 20 mg/ml of dalbavancin hydrochloride including a combination of hydroxypropyl beta cyclodextrin and NADA in 5% dextrose solution at pH 4. The table shows the data after 4 weeks at 25° C. and 40° C.

TABLE 6

Change in mannosyl aglycon impurity in a formulation with NADA and hydroxypropyl betacyclodextrin

| Composition number | Molar ratio of NADA to Dalbavancin | Molar ratio of hydroxypropyl beta cyclodextrin to Dalbavancin | pH | Time point | Δ mannosyl aglycon impurity/% |
|---|---|---|---|---|---|
| 143A | 0 | 0 | 4 | 4 weeks (40° C.) | 9.55 |
| 143A | 0 | 0 | 4 | 4 weeks (25° C.) | 1.24 |
| 143B | 1.25 | 1 | 4 | 4 weeks (40° C.) | 3.01 |
| 143B | 1.25 | 1 | 4 | 4 weeks (25° C.) | 0.21 |

Example 6

The following numbered items represent embodiments of liquid pharmaceutical formulations comprising active component.

Item 1. An aqueous formulation comprising dalbavancin or pharmaceutically acceptable salts thereof, a hydroxy propyl beta cyclodextrin solubilizing agent, an excipient selected from N-acetyl-D-amino acids, N-acetyl-glycine, and combinations thereof, wherein the pH of the aqueous formulation is in the range of 3.0 to 6.5.

Item 2. The aqueous formulation according to item 1, wherein the solution is an aqueous sterile solution.

Item 3. The aqueous formulation according to item 1 or 2, wherein the solution is an aqueous sterile solution for parenteral administration.

Item 4. The aqueous formulation according to any one of items 1 to 3, wherein the concentration of dalbavancin is in the range of 1 mg/ml to 25 mg/ml.

Item 5. The aqueous formulation according to item 4, wherein the concentration of dalbavancin is in the range of 1 mg/ml to 7 mg/ml.

Item 6. The aqueous formulation according to item 4, wherein the concentration of dalbavancin is in the range of 15 mg/ml to 22 mg/ml.

Item 7. The aqueous formulation according to item 5, wherein the concentration of dalbavancin is in the range of 2 mg/ml to 6 mg/ml.

Item 8. The aqueous formulation according to item 7, wherein the concentration of dalbavancin is in the range of 4 mg/ml to 6 mg/ml.

Item 9. The aqueous formulation according to item 6, wherein the concentration of dalbavancin is in the range of 18 mg/ml to 22 mg/ml.

Item 10. The aqueous formulation according to any one of items 1 to 9, wherein the solution has less than an 8% increase of mannosyl aglycon impurity as measured by HPLC after storage at room temperature for 3 months.

Item 11. The aqueous formulation according to any one of items 1 to 9, wherein the solution has less than a 2% increase of mannosyl aglycon impurity as measured by HPLC after storage at room temperature for 3 months.

Item 12. The aqueous formulation according to any one of item 11, wherein the solution has less than a 1.5% increase of mannosyl aglycon impurity as measured by HPLC after storage at room temperature for 3 months.

Item 13. The aqueous formulation according to any one of item 11, wherein the solution has less than a 1.0% increase of mannosyl aglycon impurity as measured by HPLC after storage at room temperature for 3 months.

Item 14. The aqueous formulation according to any one of item 11, wherein the solution has less than a 0.8% increase of mannosyl aglycon impurity as measured by HPLC after storage at room temperature for 3 months.

Item 15. The aqueous formulation according to any one of items 1 to 14, wherein the solution comprises the excipient N-Acetyl-D-Alanine.

Item 16. The aqueous formulation according to any one of items 1 to 14, wherein the solution further comprises the solubilizing agent PEG400.

Item 17. The aqueous formulation according to item 15, wherein the molar ratio of dalbavancin to N-Acetyl-D-Alanine is in the range of 1:1 to 1:40.

Item 18. The aqueous formulation according to item 17, wherein the molar ratio of dalbavancin to N-Acetyl-D-Alanine is in the range of 1:1 to 1:30.

Item 19. The aqueous formulation according to item 17, wherein the molar ratio of dalbavancin to N-Acetyl-D-Alanine is in the range of 1:1 to 1:20.

Item 20. The aqueous formulation according to item 17, wherein the molar ratio of dalbavancin to N-Acetyl-D-Alanine is in the range of 1:1 to 1:10.

Item 21. The aqueous formulation according to item 1, wherein the molar ratio of dalbavancin to hydroxypropyl beta cyclodextrin is in the range of 1:0.5 to 1:10.

Item 22. The aqueous formulation according to item 21, wherein the molar ratio of dalbavancin to hydroxypropyl beta cyclodextrin is in the range of 1:0.5 to 1:8.

Item 23. The aqueous formulation according to item 21, wherein the molar ratio of dalbavancin to hydroxypropyl beta cyclodextrin is in the range of 1:0.5 to 1:5.

Item 24. The aqueous formulation according to item 21, wherein the molar ratio of dalbavancin to hydroxypropyl beta cyclodextrin is in the range of 1:0.5 to 1:6.

Item 25. The aqueous formulation according to item 21, wherein the molar ratio of dalbavancin to hydroxypropyl beta cyclodextrin is in the range of 1:0.5 to 1:4.

Item 26. The aqueous formulation according to item 1, wherein pH of the formulation is in the range of 3.5 to 6.0.

Item 27. The aqueous formulation according to item 26, wherein pH of the formulation is in the range of 3.5 to 5.5.

Item 28. The aqueous formulation according to item 26, wherein pH of the formulation is in the range of 3.5 to 5.0.

Item 29. The aqueous formulation according to item 26, wherein pH of the formulation is in the range of 3.5 to 4.5.

Item 30. An aqueous formulation consisting of dalbavancin or pharmaceutically acceptable salts thereof, a hydroxy propyl beta cyclodextrin solubilizing agent, an excipient selected from N-acetyl-D-amino acids, N-acetyl-glycine, and combinations thereof, wherein the pH of the aqueous formulation is in the range of 3.0 to 6.5.

Item 31. The aqueous formulation according to item 30, wherein the solution is an aqueous sterile solution.

Item 32. The aqueous formulation according to item 30 or 31, wherein the solution is an aqueous sterile solution for parenteral administration.

Item 33. The aqueous formulation according to any one of items 30 to 32, wherein the concentration of dalbavancin is in the range of 1 mg/ml to 25 mg/ml.

Item 34. The aqueous formulation according to item 33, wherein the concentration of dalbavancin is in the range of 1 mg/ml to 7 mg/ml.

Item 35. The aqueous formulation according to item 33, wherein the concentration of dalbavancin is in the range of 15 mg/ml to 22 mg/ml.

Item 36. The aqueous formulation according to item 34, wherein the concentration of dalbavancin is in the range of 2 mg/ml to 6 mg/ml.

Item 37. The aqueous formulation according to item 36, wherein the concentration of dalbavancin is in the range of 4 mg/ml to 6 mg/ml.

Item 38. The aqueous formulation according to item 35, wherein the concentration of dalbavancin is in the range of 18 mg/ml to 22 mg/ml.

Item 39. The aqueous formulation according to any one of items 30 to 38, wherein the solution has less than an 8% increase of the mannosyl aglycon impurity as measured by HPLC after storage at room temperature for 3 months.

Item 40. The aqueous formulation according to any one of items 30 to 38, wherein the solution has less than a 2% increase of the mannosyl aglycon impurity as measured by HPLC after storage at room temperature for 3 months.

Item 41. The aqueous formulation according to any one of item 40, wherein the solution has less than a 1.5% increase of the mannosyl aglycon impurity as measured by HPLC after storage at room temperature for 3 months.

Item 42. The aqueous formulation according to any one of item 40, wherein the solution has less than a 1.0% increase of the mannosyl aglycon impurity as measured by HPLC after storage at room temperature for 3 months.

Item 43. The aqueous formulation according to any one of item 40, wherein the solution has less than a 0.8% increase of the mannosyl aglycon impurity as measured by HPLC after storage at room temperature for 3 months.

Item 44. The aqueous formulation according to any one of items 301 to 43, wherein the solution comprises the excipient N-Acetyl-D-Alanine.

Item 45. The aqueous formulation according to any one of items 30 to 43, wherein the solution further comprises the solubilizing agent PEG400.

Item 46. The aqueous formulation according to item 44, wherein the molar ratio of dalbavancin to N-Acetyl-D-Alanine is in the range of 1:1 to1:40.

Item 47. The aqueous formulation according to item 46, wherein the molar ratio of dalbavancin to N-Acetyl-D-Alanine is in the range of 1:1 to1:30.

Item 48. The aqueous formulation according to item 46, wherein the molar ratio of dalbavancin to N-Acetyl-D-Alanine is in the range of 1:1 to1:20.

Item 49. The aqueous formulation according to item 46, wherein the molar ratio of dalbavancin to N-Acetyl-D-Alanine is in the range of 1:1 to1:10.

Item 50. The aqueous formulation according to item 30, wherein the molar ratio of dalbavancin to hydroxypropyl beta cyclodextrin is in the range of 1:0.5 to 1:10.

Item 51. The aqueous formulation according to item 50, wherein the molar ratio of dalbavancin to hydroxypropyl beta cyclodextrin is in the range of 1:0.5 to 1:8.

Item 52. The aqueous formulation according to item 50, wherein the molar ratio of dalbavancin to hydroxypropyl beta cyclodextrin is in the range of 1:0.5 to 1:5.

Item 53. The aqueous formulation according to item 50, wherein the molar ratio of dalbavancin to hydroxypropyl beta cyclodextrin is in the range of 1:0.5 to 1:6.

Item 54. The aqueous formulation according to item 50, wherein the molar ratio of dalbavancin to hydroxypropyl beta cyclodextrin is in the range of 1:0.5 to 1:4.

Item 55. The aqueous formulation according to item30, wherein pH of the solution is in the range of 3.5 to 6.0.

Item 56. The aqueous formulation according to item 55, wherein pH of the solution is in the range of 3.5 to 5.5.

Item 57. The aqueous formulation according to item 55, wherein pH of the solution is in the range of 3.5 to 5.0.

Item 58. The aqueous formulation according to item 55, wherein pH of the solution is in the range of 3.5 to 4.5.

Item 59. The aqueous formulation according to items 1 to 58, wherein the formulation further comprises dextrose.

Item 60. A method of treatment of an acute bacterial infection caused by *Staphylococcus aureus, Streptococcus pyogenes, Streptococcus agalactiae, Streptococcus dysgalactiae, Streptococcus anginosus* group or vancomycin susceptible isolates of *Enterococcus faecalis* comprising the step of administering the aqueous formulation as defined in items 1 to 59 to a patient in need thereof.

Item 61. The aqueous formulation as defined in items 1 to 59 for use in treatment of acute bacterial infections caused by *Staphylococcus aureus, Streptococcus pyogenes, Streptococcus agalactiae, Streptococcus dysgalactiae, Streptococcus anginosus* group or vancomycin susceptible isolates of *Enterococcus faecalis*.

Item 62. A method of manufacturing an aqueous dalbavancin formulation defined in items 1 to 59, comprising the steps of mixing dalbavancin or the pharmaceutically acceptable salt thereof and at least one excipient selected from N-acetyl-D-amino acids or N-acetyl-glycine and a hydroxy propyl beta cyclodextrin solubilizing agent with water, wherein the pH in the solution is in the range of 3.0 to 6.5.

Item 63. An aqueous formulation, comprising dalbavancin or pharmaceutically acceptable salts thereof, and a hydroxypropyl beta cyclodextrin solubilizing agent, wherein the pH in the solution is in the range of 3.0 to 6.5.

Item 64. The aqueous formulation according to item 63, wherein the solution is an aqueous sterile solution.

Item 65. The aqueous formulation according to item 63 or 64, wherein the formulation is an aqueous sterile formulation for parenteral administration.

Item 66. The aqueous formulation according to any one of items 63 to 65, wherein the concentration of dalbavancin is in the range 1 mg/ml to 25 mg/ml.

Item 67. The aqueous formulation according to item 66, wherein the concentration of dalbavancin is in the range of 1 mg/ml to 7 mg/ml.

Item 68. The aqueous formulation according to item 66, wherein the concentration of dalbavancin is in the range of 15 mg/ml to 22 mg/ml.

Item 69. The aqueous formulation according to item 67, wherein the concentration of dalbavancin is in the range of 2 mg/ml to 6 mg/ml.

Item 70. The aqueous formulation according to item 69, wherein the concentration of dalbavancin is in the range of 4 mg/ml to 6 mg/ml.

Item 71. The aqueous formulation according to item 68, wherein the concentration of dalbavancin is in the range of 18 mg/ml to 22 mg/ml.

Item 72. The aqueous formulation according to any one of items 63 to 71, wherein the formulation has less than an 8% increase of the mannosyl aglycon impurity as measured by HPLC after storage at room temperature for 3 months.

Item 73. The aqueous formulation according to any one of items 63 to 71, wherein the formulation has less than a 2% increase of the mannosyl aglycon impurity as measured by HPLC after storage at room temperature for 3 months.

Item 74. The aqueous formulation according to any one of item 73, wherein the formulation has less than a 1.5% increase of the mannosyl aglycon impurity as measured by HPLC after storage at room temperature for 3 months.

Item 75. The aqueous formulation according to any one of item 73, wherein the formulation has less than a 1.0% increase of the mannosyl aglycon impurity as measured by HPLC after storage at room temperature for 3 months.

Item 76. The aqueous formulation according to any one of item 73, wherein the formulation has less than a 0.8% increase of the mannosyl aglycon impurity as measured by HPLC after storage at room temperature for 3 months.

Item 77. The aqueous formulation according to item 63, wherein the molar ratio of dalbavancin to hydroxypropyl beta cyclodextrin is in the range of 1:0.5 to 1:10.

Item 78. The aqueous formulation according to item 77, wherein the molar ratio of dalbavancin to hydroxypropyl beta cyclodextrin is in the range of 1:0.5 to 1:8.

Item 79. The aqueous formulation according to item 77, wherein the molar ratio of dalbavancin to hydroxypropyl beta cyclodextrin is in the range of 1:0.5 to 1:5.

Item 80. The aqueous formulation according to item 77, wherein the molar ratio of dalbavancin to hydroxypropyl beta cyclodextrin is in the range of 1:0.5 to 1:6.

Item 81. The aqueous formulation according to item 77, wherein the molar ratio of dalbavancin to hydroxypropyl beta cyclodextrin is in the range of 1:0.5 to 1:4.

Item 82. The aqueous formulation according to item 77, wherein the molar ratio of dalbavancin to hydroxypropyl beta cyclodextrin is in the range of 1:0.6 to 1:2.

Item 83. The aqueous formulation according to item 77, wherein the molar ratio of dalbavancin to hydroxypropyl beta cyclodextrin is in the range of 1:0.6 to 1:1.

Item 84. The aqueous formulation according to item 77, wherein the molar ratio of dalbavancin to hydroxypropyl beta cyclodextrin is in the range of 1:0.7 to 1:0.9.

Item 85. The aqueous formulation according to item 66, wherein pH of the solution is in the range of 3.5 to 6.0.

Item 86. The aqueous formulation according to item 85, wherein pH of the solution is in the range of 3.5 to 5.5.

Item 87. The aqueous formulation according to item 85, wherein pH of the solution is in the range of 3.5 to 5.0.

Item 88. The aqueous formulation according to item 85, wherein pH of the solution is in the range of 3.5 to 4.5.

Item 89. The aqueous formulation according to items 63 to 88, wherein the formulation further comprises dextrose.

Item 90. A method of treatment of an acute bacterial infection caused by *Staphylococcus aureus, Streptococcus pyogenes, Streptococcus agalactiae, Streptococcus dysgalactiae, Streptococcus anginosus* group or vancomycin susceptible isolates of *Enterococcus faecalis* comprising the step of administering the aqueous formulation as defined in items 63 to 89 to a patient in need thereof.

Item 91. The aqueous formulation as defined in items 63 to 89 for use in treatment of acute bacterial infections caused by *Staphylococcus aureus, Streptococcus pyogenes, Streptococcus agalactiae, Streptococcus dysgalactiae, Streptococcus anginosus* group or vancomycin susceptible isolates of *Enterococcus faecalis*.

Item 92. A method of manufacturing an aqueous dalbavancin formulation defined in items 63 to 89, comprising the steps of mixing dalbavancin or the pharmaceutically acceptable salt thereof and the hydroxypropyl beta cyclodextrin solubilizing agent with water, wherein the pH in the solution is in the range of 3.0 to 6.5.

Item 93. A method of manufacturing an aqueous dalbavancin formulation according to item 62 and item 92, wherein the formulation is further sterile filtered.

The invention claimed is:

1. An aqueous formulation, comprising dalbavancin or a pharmaceutically acceptable salt thereof, and hydroxypropyl beta cyclodextrin, wherein the concentration of dalbavancin is 1 mg/ml to 7 mg/ml, the molar ratio of dalbavancin to hydroxypropyl beta cyclodextrin is 1:0.5 to 1:2, the pH in the formulation is 3.5 to 4.5, and wherein the formulation does not comprise a buffer.

2. The aqueous formulation according to claim 1, wherein the aqueous formulation is an aqueous sterile solution.

3. The aqueous formulation according to claim 1, wherein the formulation is an aqueous sterile formulation for parenteral administration.

4. The aqueous formulation according to claim 1, wherein the concentration of dalbavancin is 32 mg/ml to 6 mg/ml.

5. The aqueous formulation according to claim 4, wherein the concentration of dalbavancin is 4 mg/ml to 6 mg/ml.

6. The aqueous formulation according to claim 1, wherein the formulation has less than an 8% increase of mannosyl aglycon impurity after storage at room temperature for 3 months, as measured by high performance liquid chromatography (HPLC).

7. The aqueous formulation according to claim 1, wherein the formulation has less than a 2% increase of mannosyl aglycon impurity after storage at room temperature for 3 months, as measured by HPLC.

8. The aqueous formulation according to claim 1, wherein the formulation further comprises dextrose.

9. A method of treatment of an acute bacterial infection caused by *Staphylococcus aureus, Streptococcus pyogenes, Streptococcus agalactiae, Streptococcus dysgalactiae, Streptococcus anginosus* group bacteria, or vancomycin susceptible isolates of *Enterococcus faecalis* in a patient in need thereof comprising administering the aqueous formulation as defined in claim 1 to the patient.

* * * * *